(12) United States Patent
Baek et al.

(10) Patent No.: US 10,161,006 B2
(45) Date of Patent: Dec. 25, 2018

(54) DIAGNOSIS OF HEMATOLOGIC DISEASES

(71) Applicant: IUCF-HYU (INDUSTRY-UNIVERSITY COOPERATION FOUNDATION HANYANG UNIVERSITY), Seongdong-gu (KR)

(72) Inventors: Eun Jung Baek, Seocho-gu (KR); Eun-Mi Lee, Guri-si (KR)

(73) Assignee: IUCF-HYU (INDUSTRY-UNIVERSITY COOPERATION FOUNDATION HANYANG UNIVERSITY), Seongdong-gu (KR)

( * ) Notice: Subject to any disclaimer, the term of this patent is extended or adjusted under 35 U.S.C. 154(b) by 60 days.

(21) Appl. No.: 15/125,087

(22) PCT Filed: Mar. 11, 2015

(86) PCT No.: PCT/KR2015/002378
§ 371 (c)(1),
(2) Date: Sep. 9, 2016

(87) PCT Pub. No.: WO2015/137738
PCT Pub. Date: Sep. 17, 2015

(65) Prior Publication Data
US 2017/0114408 A1    Apr. 27, 2017

(30) Foreign Application Priority Data
Mar. 11, 2014  (KR) .................. 10-2014-0028399

(51) Int. Cl.
*C07H 21/04* (2006.01)
*C12Q 1/68* (2018.01)
*C12Q 1/6883* (2018.01)
*C12Q 1/6886* (2018.01)
*G01N 33/574* (2006.01)
*G01N 33/68* (2006.01)

(52) U.S. Cl.
CPC ......... *C12Q 1/6883* (2013.01); *C12Q 1/6886* (2013.01); *G01N 33/57426* (2013.01); *G01N 33/6893* (2013.01); *C12Q 2600/118* (2013.01); *C12Q 2600/158* (2013.01); *G01N 2333/47* (2013.01)

(58) Field of Classification Search
None
See application file for complete search history.

(56) References Cited
U.S. PATENT DOCUMENTS

| | | | |
|---|---|---|---|
| 8,198,094 B2 | 6/2012 | Stossel et al. | |
| 8,440,622 B2 | 5/2013 | Stossel et al. | |
| 2007/0072178 A1* | 3/2007 | Haferlach | C12Q 1/6886 435/6.16 |
| 2010/0021428 A1 | 1/2010 | Stossel et al. | |
| 2010/0227807 A1 | 9/2010 | Stossel et al. | |
| 2012/0208743 A1 | 8/2012 | Stossel et al. | |
| 2013/0230455 A1 | 9/2013 | Stossel et al. | |

FOREIGN PATENT DOCUMENTS

| | | |
|---|---|---|
| JP | 2012-53071 A | 3/2012 |
| JP | 2012-83359 A | 4/2012 |
| WO | WO 2010/105160 A2 | 9/2010 |

OTHER PUBLICATIONS

Qi et al. (Genetics and Molecules Research, vol. 7, No. 2, pp. 379-387, 2008) (Year: 2008).*
Qian et al. (Oncology Reports, vol. 14, pp. 1189-1197, 2005). (Year: 2005).*
Cobb et al. (Ann Surg. vol. 250, No. 4, pp. 531-539, Oct. 2009) (Year: 2009).*
Robinson et al. (RNA, vol. 18, pp. 1435-1445, 2012). (Year: 2012).*
Barzi et al.—"Myelodysplastic syndromes: A practical approach to diagnosis and treatment", Cleveland Clinic Journal of Medicine, vol. 77, No. 1, Jan. 2010, pp. 37-44.
Brunning et al.—"Myelodysplastic syndromes/neoplasms overview", WHO Classification of Tumours of Haematopoietic and Lymphoid Tissues, 3 pages.
Chauhan et al.—"Anti-amyloidogenic, anti-oxidant and anti-apoptotic role of gelsolin in Alzheimer's disease" Biogerontology (2008), 9, pp. 381-389.
Choi et al.—"Autonomous control of terminal erythropoiesis via physical interactions among erythroid cells", Stem Cell Research (2013), 10, pp. 442-453.
Gremm et al.—"Gelsolin as a calcium-regulated actin filament-capping protein", Eur. J. Biochem., 267, pp. 4339-4345 FEBS 2000, pp. 4339-4345.
Hofmann et al.—"Characterization of gene expression of CD34+ cells from normal and myelodysplastic bone marrow", Blood Nov. 15, 2002, vol. 100, No. 10, pp. 3553-3560.
Lee et al.—"The Extracellular Actin-Scavenger System and Actin Toxicity", Mechanisms of Disease, vol. 326, No. 20, pp. 1335-1341.
Newman et al.—"Revisiting Use of Growth Factors in Myelodysplastic Syndromes". Asian Pacific Journal of Cancer Prevention, vol. 13, 2012, pp. 1081-1091.
Noske et al.—"Loss of Gelsolin expression in human ovarian carcinomas" European Journal of Cancer 41 (2005), pp. 461-469.
Suhler et al.—"Decreased plasma gelsolin concentrations in acute liver failure, myocardial infarction, septic shock, and myonecrosis", Critical Care Medicine, vol. 25(4), Apr. 1997.
Vardiman et al.—"Introduction and overview of the classification of the myeloid neoplasms" WHO Classification of Tumours of Haematopoietic and Lymphoid Tissues, 2 pages.

(Continued)

*Primary Examiner* — Jeanine A Goldberg
(74) *Attorney, Agent, or Firm* — Oblon, McClelland, Maier & Neustadt, L.L.P.

(57) ABSTRACT

The present invention relates to a method for screening a risk group of a hematologic disease and a method for analyzing the prognosis of a hematologic disease based on the measurement of the level of gelsolin mRNA in buffy coat of peripheral blood or a bone marrow aspirate. The use of the present invention enables the screening of a risk group of a hematologic disease and the analysis of prognosis of a patient with a hematologic disease in an easy and accurate manner.

3 Claims, 7 Drawing Sheets

Specification includes a Sequence Listing.

(56) References Cited

OTHER PUBLICATIONS

International Search Report dated May 7, 2015 in PCT/KR2015/002378.
Reza Shirkoohi, et al., "Gelsolin Induces Promonocytic Leukemia Differentiation Accompanied by Upregulation of p21CIP1", Asian Pacific Journal of Cancer Prevention, vol. 13, No. 9, 2012, pp. 4827-4834.
Claudio Cantù, et al., "Defective erythroid maturation in gelsolin mutant mice", Haematologica, vol. 97, No. 7, 2012, pp. 980-988.
DiNubile, Mark J., et al. "Prognostic implications of declining plasma gelsolin levels after allogeneic stem cell transplantation." Blood 100.13 (2002):4367-4371.†
Braoudaki, Maria, et al. "Protein biomarkers distinguish between high-and low-risk pediatric acute lymphoblastic leukemia in a tissue specific manner." Journal of Hematology & Oncology 6.1 (2013): 52.†
Kwiatkowski, David J. "Predominant induction of gelsolin and actin-binding protein during myeloid differentiation." Journal of Biological Chemistry 263.27 (1988): 13857-13862.†

\* cited by examiner
† cited by third party

[Fig. 1]
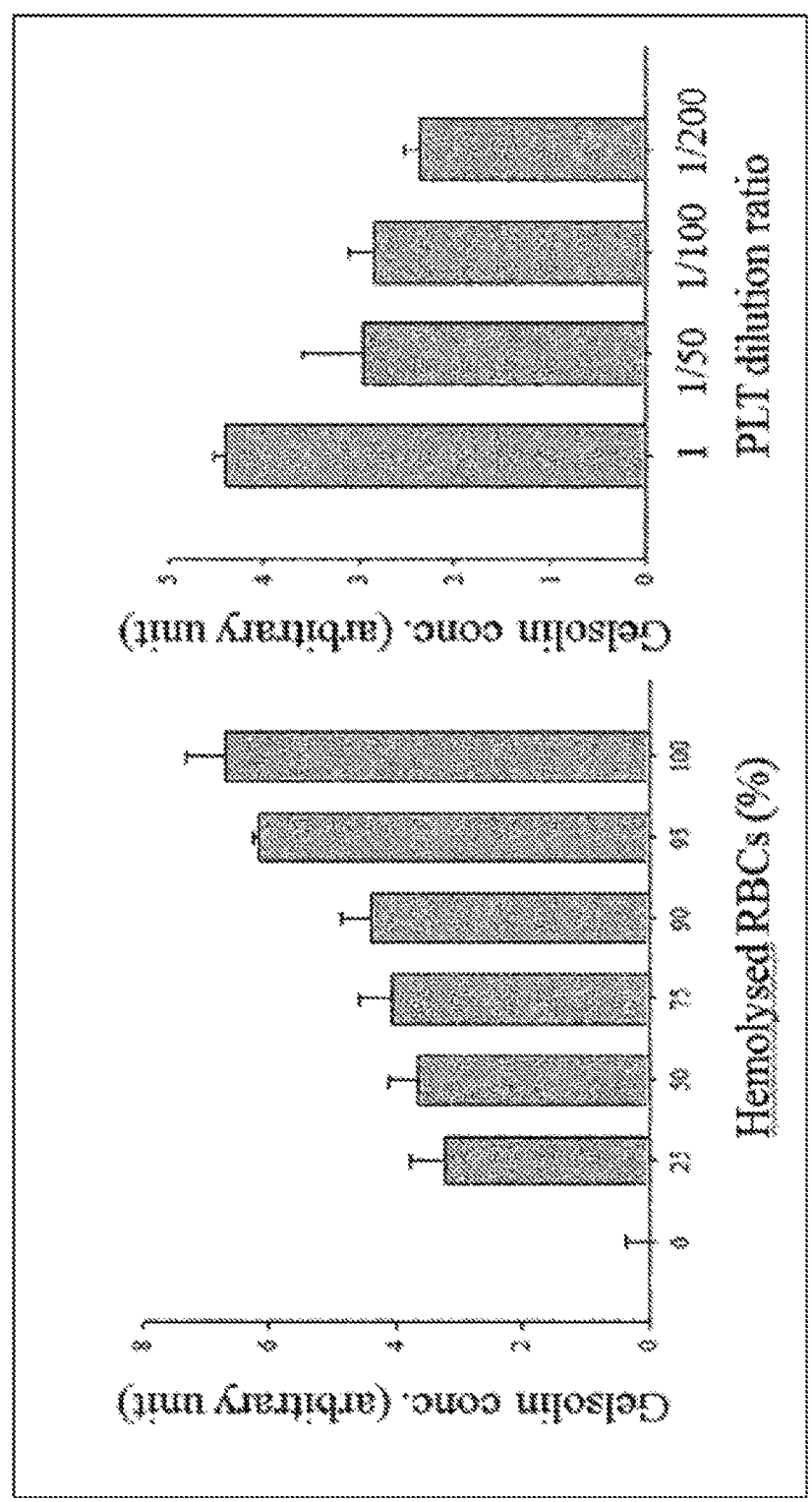

[Fig. 2]
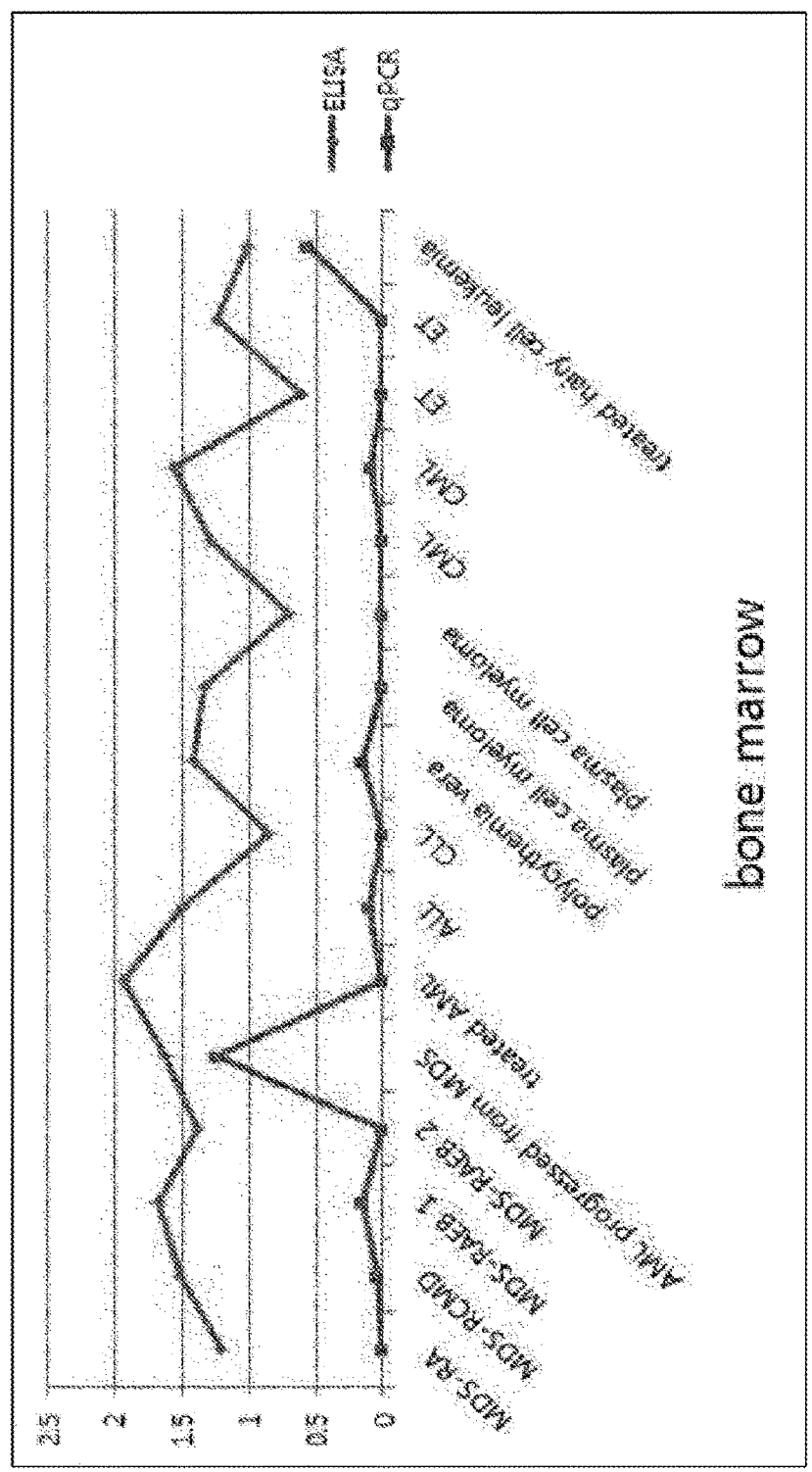

[Fig. 3]
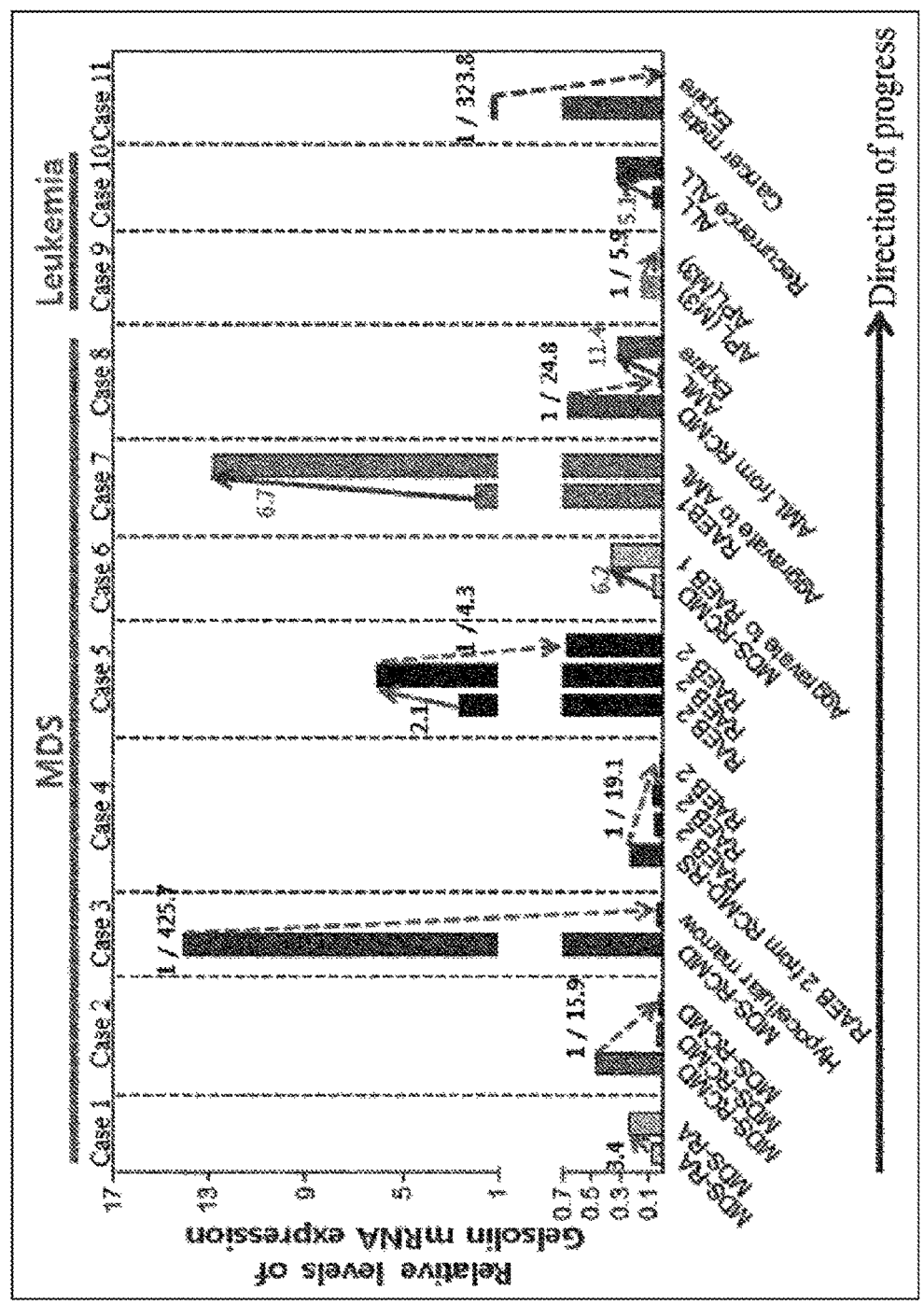

[Fig. 4]
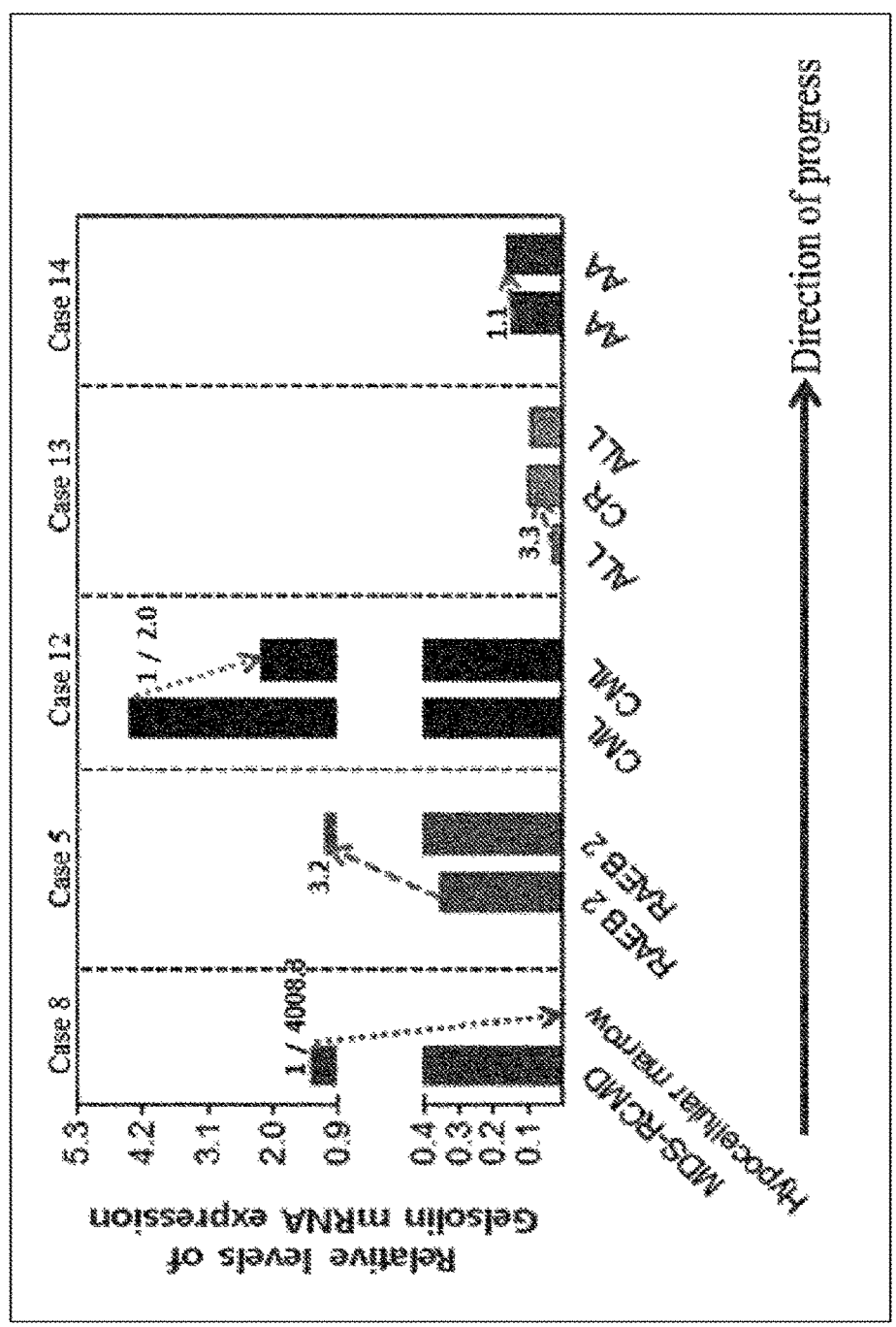

[Fig. 5]
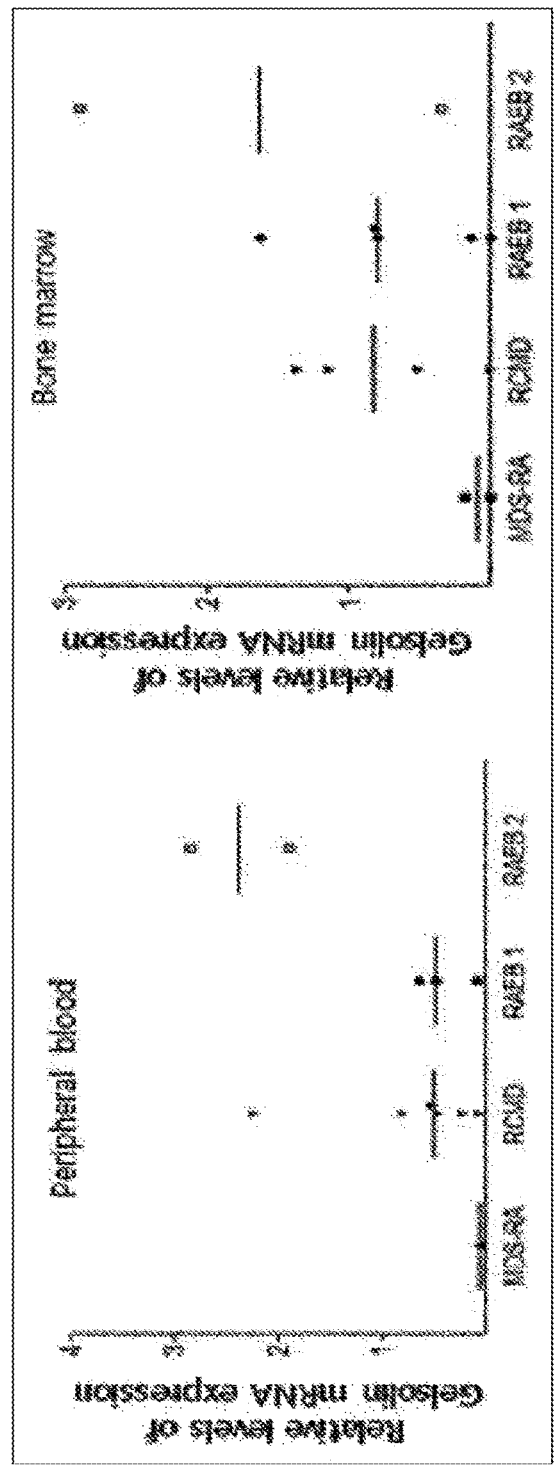

[Fig. 6]
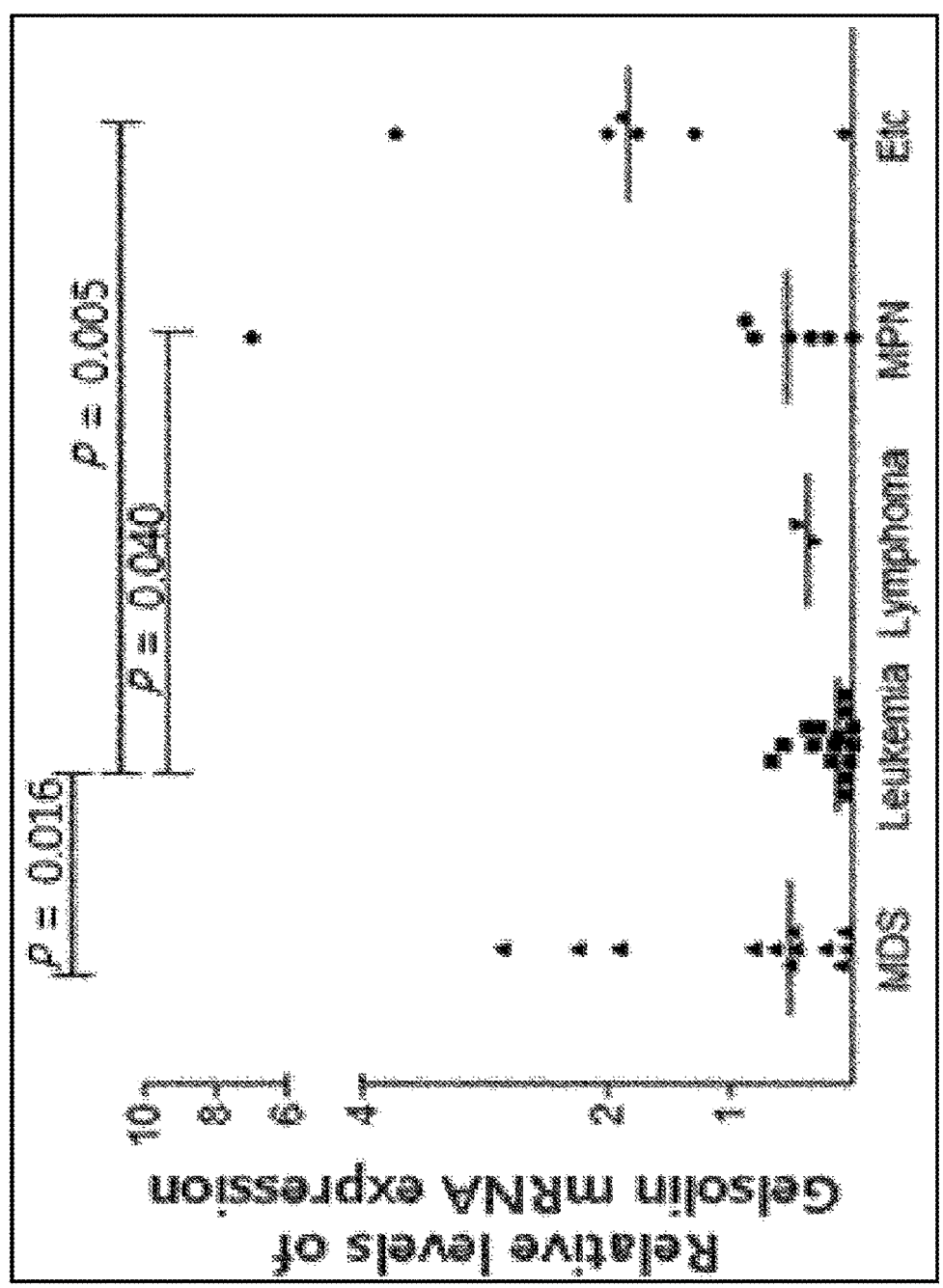

[Fig. 7]
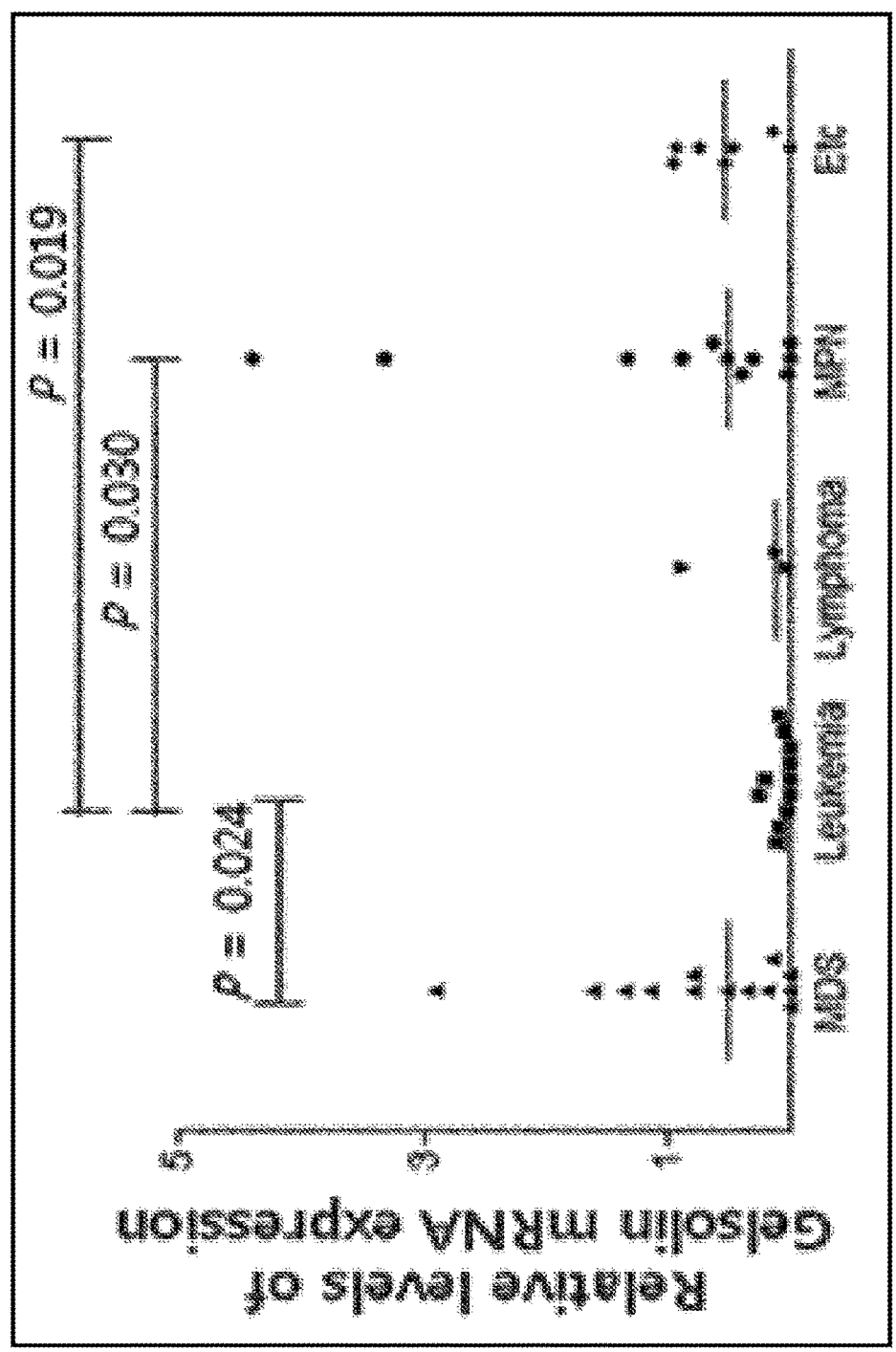

DIAGNOSIS OF HEMATOLOGIC DISEASES

TECHNICAL FIELD

The present invention was supported by the Ministry of Health and Welfare of the Republic of Korea under Project No. HI10C17400200, which was conducted in the research project entitled "Advanced medical technology development" within the project named "Research on efficient differentiation and mechanism of stem cells into erythroid progenitor cells" by the Industry-Academic Cooperation Foundation, Yonsei University under the management of the Korea Health Industry Development Institute, from Apr. 1, 2013 to Mar. 31, 2014.

The present invention was also supported by the Ministry of Health and Welfare of Republic of Korea under Project No. HI12C0202, which was conducted in the research project entitled "Advanced medical technology development" within the project named "Development of drugs for myelodysplastic syndrome through induction of stem cell differentiation and maturation" by the Industry-Academic Cooperation Foundation, Hanyang University, under the management of the Korea Health Industry Development Institute, from Aug. 1, 2013 to Jul. 31, 2014.

This application claims the benefit of priority to Korean Patent Application No. 10-2014-0028399, filed on Mar. 11, 2014, the disclosure of which is incorporated herein by reference.

The present invention relates to a method for screening a risk group of a hematologic disease and a method for analyzing the prognosis of a hematologic disease based on the measurement of the level of gelsolin mRNA in buffy coat.

BACKGROUND ART

Hematologic Neoplastic Diseases

Hematologic neoplastic diseases of the blood and bone marrow are broadly categorized into acute/chronic leukemias, myeloproliferative neoplasms (MPN), and myelodysplastic syndromes (MDS) (Vardiman J W 2008).

Acute/chronic leukemias are subdivided into myelogenous leukemia and lymphocytic leukemia.

Myeloproliferative neoplasms are subdivided into chronic myelogenous leukemia (CML), polycythemia vera (P. vera), essential thrombocythemia (ET), primary myelofibrosis (PMF), and others.

Myelodysplastic syndromes (MDS) are subdivided into refractory cytopenia with unilineage dysplasia (RCUD), refractory cytopenia with multilineage dysplasia (RCMD), refractory anemia with excess blasts (RAEB-1 is defined as having 5-10% myeloblasts and RAEB-2 is defined as having 11-19% myeloblasts in the bone marrow) (Brunning R D 2008).

Explanation of Myelodysplastic Syndromes, Prevalence

Myelodysplastic syndromes are acquired, rare, incurable hematologic diseases characterized by inefficient hematopoiesis due to progressive pancytopenia and abnormal cell differentiation/maturation. These diseases often show chronic propagation over several years and transform into acute leukemia. For these reasons, myelodysplastic syndromes are sometimes called preleukemias.

Myelodysplastic syndromes are primary tumors of bone marrow and their incidence is higher than that of general leukemias. However, the incidence of myelodysplastic syndromes is currently underestimated and it is estimated that many patients are not diagnosed as having myelodysplastic syndromes. Based on the statistical data from the National Health Insurance Corporation, Republic of Korea, 1,845 domestic patients suffered from myelodysplastic syndromes in 2005 and 500-600 new patients are diagnosed as myelodysplastic syndromes annually in Korea. In the United States, the incidence of myelodysplastic syndromes is 1 per 500 individuals over the age of 60 (Newman, Maness-Harris et al. 2012) and 15,000 new patients with myelodysplastic syndromes are found annually and the number is estimated to rise sharply (Barzi and Sekeres 2010).

Diagnostic Methods, Prognosis

Myelodysplastic syndromes are diagnosed based on peripheral blood or bone marrow examination. The degrees of dysplasia are evaluated based on three classifications of hemocytoblasts in the bone marrow, i.e. three different lineages of myeloid cells, erythroid cells, and platelet-forming megakaryocytes, to determine their range and severity. Patients with myelodysplastic syndromes survive for an average of only 22 months, which is similar to the median survival of lung cancer patients, and have a poor 4-5.7-year prognosis. Refractory cytopenia with unilineage dysplasia (RCUD) and refractory anemia with ring sideroblasts (RARS) belong to low risk groups with relatively good prognosis. In contrast, refractory cytopenia with multilineage dysplasia (RCMD) and refractory anemia with excess blasts (RAEB-1 and RAEB-2) that progress to acute leukemia within 9-30 months or reach death belong to groups with poor prognosis. 25% of cases of RAEB-1 and 33% of cases of RAEB-2 progress to AML. Indicators capable of continuously predicting the conditions of patients with these diseases have never been, to our knowledge, reported to date.

Current Therapies for Myelodysplastic Syndromes

At present, there are no effective therapeutic agents for myelodysplastic syndromes. For this reason, patients at the initial stage of the diseases are receiving no suitable treatment for their diseases from the hospital. When the diseases become worse, the patients receive traditional supportive care. Anticancer chemotherapy and allogenic hematopoietic stem cell transplantation are performed in the patients at higher risk.

Over the past 5 years, new concepts of epigenetics have led to an improvement in viability and are thus considered new therapies capable of replacing the best supportive care, which has been a therapeutic principle until now. Continued efforts have been made to develop combination therapies with various drugs. However, the proportion of patients responding to therapeutic agents for myelodysplastic syndromes does not exceed an average of 10% for even the best therapeutic agent. Thus, there is a need in the near future to develop fundamental therapeutic agents in response to the causes of myelodysplastic syndromes and safe therapeutic agents/auxiliary therapeutic agents that are free from side effects caused by protein irritations instead of hematopoietic stem cell transplantation that is substantially impossible to implement on aged patients.

Under these circumstances, the present inventors have found that the dysplasia of erythroid cells caused by culture of bone marrow cells and ex vivo culture of hematopoietic stem cells from patients with myelodysplastic syndromes can be effectively suppressed by treatment of the culture with a human recombinant gelsolin protein. Based on this finding, the present inventors have investigated the possible use of the plasma or intracellular levels of gelsolin as diagnostic and prognostic markers for hematologic neoplastic diseases, including myelodysplastic syndromes.

Gelsolin

Gelsolin is an actin filament-binding protein and is known to cut or cap actin filaments to regulate actin assembly or disassembly (Gremm and Wegner 2000). Gelsolin exists in two forms, cytoplasmic or plasma. Plasma gelsolin differs from cytoplasmic gelsolin by the addition of 25 amino acids to the N-terminus of the molecule (Chauhan, Ji et al. 2008). Plasma gelsolin is secreted from the cell. Gelsolin is present at a high concentration of 200-250 mg/L in normal plasma (Kwiatkowski 1988). Plasma gelsolin is an actin-scavenging protein. When cellular tissue is injured, plasma gelsolin isolates and removes considerable amounts of G-actin and F-actin released into the plasma to protect the microcirculation (Lee and Galbraith 1992).

Diagnostic Values of Gelsolin in Other Diseases

In recent years, a great deal of research has been conducted on the relationship between plasma gelsolin and disease. Plasma gelsolin is mainly produced in and secreted from muscles (Kwiatkowski 1988) and has been investigated in various diseases, such as burns, trauma, brain ischemia/stroke, and respiratory failure. In some disease groups (acute lung injury, septic shock, trauma, and myonecrosis groups) associated with acute cellular injuries and necrosis, the gelsolin values decrease to about 50% of the normal value (Suhler, Lin et al. 1997), and as a result, defense systems by the actin-scavenger system fail to work, which also fatally affects the prognosis of the patients. Decreased gelsolin expression in various tumors, such as colorectal cancer, gastric cancer, lung cancer, ovarian cancer, breast cancer, bladder cancer, prostate cancer, and renal cancer, was reported to be closely associated with carcinogenesis (Noske, Denkert et al. 2005).

Diagnostic Values of Gelsolin mRNA Level in Myelodysplastic Syndromes

Little is known about the relevance of gelsolin in myelodysplastic syndrome (MDS) patients. Most previous studies have reported the measurement of decreased plasma gelsolin by ELISA and Western blotting but did not verify the suitability for the detection techniques. The measurement of plasma protein levels in acute or chronic leukemia patients was reported but no report has appeared on an increase or decrease of gelsolin at a molecular level.

The results of gene array in bone marrow mononuclear cells of patients with myelodysplastic syndromes (MDS) and patients with bone marrow disease showed patterns of decreasing gelsolin expression (Qi, Chen et al. 2008, Genetics and Molecular Research). However, the expression of each gene was not identified or verified by PCR based on the array results. Further, the mononuclear cells do not reflect the entire cell situation due to the absence of polymorphonuclear cells, which are found only in platelets and buffy coat. Moreover, the mononuclear cells obtained through long-term manual work with ficoll cannot be practically used in a large quantity in environments for patient diagnosis, making it difficult to use as biomarkers. Bone marrow examination is performed only for initial diagnosis and is not useful for prognosis and follow-up. Furthermore, the role of the mononuclear cells as prognostic markers upon follow-up and diagnosis of patients with hematologic tumors remains unknown.

The presence of gelsolin at a low concentration in the bone marrow and peripheral blood serum of acute myeloblastic leukemia patients was confirmed by protein quantitative analysis based on 2-dimensional gel electrophoresis (2DE) (Braoudaki, Lambrou et al. 2013). However, the reasons for an increase in mRNA signal in response to a certain intracellular demand for gelsolin production, the proportion of intracytoplasinic gelsolin or plasma gelsolin produced, and the degradation of secreted gelsolin into extracellular fluids (blood plasma) are not fully understood, making it difficult to predict the correlation between mRNA and plasma gelsolin level.

Most of the current papers on plasma gelsolin in patient groups by ELISA and Western blotting techniques fail to exclude hemolysis of blood samples and overlook the release of intracellular gelsolin into plasma upon hemolysis of samples, making it impossible to measure the exact amount of gelsolin. Also in the case where mononuclear cells are isolated from whole blood samples, a considerable amount of RBCs and platelets are difficult to remove from mononuclear cells. As a result, it is impossible to exclude the effect of gelsolin present at a high concentration in the platelets. No study about gelsolin levels has been reported in sample with erythrocytes and platelets included. There has been no report checking plasma gelsolin level affected by hemolysis in blood.

The present inventors have investigated gelsolin gene expression in bone marrow and peripheral blood of patients with hematologic neoplastic diseases in order to determine the possible use of gelsolin as a factor for the diagnosis and progression of the diseases or a prognostic factor for the diseases. To this end, the present inventors have conducted various experiments to determine whether there are problems in gelsolin expression in patients with myelodysplastic syndromes and various hematologic neoplastic diseases and whether to use the levels of intracytoplasmic protein and mRNA in bone marrow and peripheral blood samples as markers for hematologic neoplastic diseases through various experiments.

Papers and patent publications are referenced and cited throughout the specification, the disclosure of which is incorporated herein by reference in its entirety in order to more clearly disclose the invention and the state of the art to which the invention pertains.

The present inventors have earnestly and intensively conducted research to develop a method for diagnosing hematologic diseases and a method for analyzing the prognosis of hematologic diseases using novel diagnostic markers that are not affected by the levels of platelets and the hemolysis of erythrocytes in subjects, and as a result, have succeeded in diagnosing hematologic diseases and analyzing the prognosis of the diseases by measuring the levels of gelsolin mRNA in peripheral blood or bone marrow from the subjects, accomplishing the present invention.

Therefore, it is one object of the present invention to provide a method for screening a risk group of a hematologic disease.

It is another further object of the present invention to provide a method for analyzing the prognosis of a hematologic disease.

Other objects and advantages of the invention will become more apparent from the following detailed description, claims, and drawings.

According to one aspect of the present invention, there is provided a method for screening a risk group of a hematologic disease, including (a) providing buffy coat of peripheral blood or a bone marrow aspirate isolated from a subject and (b) measuring the expression level of gelsolin mRNA in the buffy coat as a marker for a hematologic disease wherein when the expression level of gelsolin mRNA is measured to be as low as 80% or less or as high as 120% or more of that in a normal group, the subject is diagnosed as being at risk of the hematologic disease.

The present inventors have earnestly and intensively conducted research to develop a method for diagnosing hematologic diseases and a method for analyzing the prognosis of hematologic diseases using novel diagnostic markers that are not affected by the levels of platelets and the homolysis of erythrocytes in subjects, and as a result, have succeeded in diagnosing hematologic diseases, including aplastic anemia and hematologic neoplastic diseases, and analyzing the prognosis of the diseases by measuring the levels of gelsolin mRNA in peripheral blood or bone marrow from the subjects, accomplishing the present invention.

The individual steps of the method will be explained in detail.

(a) Provision of Buffy Coat of Peripheral Blood or a Bone Marrow Aspirate Isolated from a Subject The diagnostic method of the present invention uses buffy coat of peripheral blood or a bone marrow aspirate isolated from a subject. As used herein, the term "peripheral blood" means blood that circulates systematically and can be collected through the skin. As used herein, the term "bone marrow aspirate" is a soft tissue located in the inner cavity of the bone and refers to a biological sample extracted from bone marrow as a hematopoietic organ by a suitable aspiration method known in the art. For convenience, the terms "bone marrow aspirate" and "bone marrow" are used interchangeably herein. The peripheral blood or bone marrow aspirate is isolated from a subject before use. The bone marrow aspirate is preferably used for initial diagnosis but its isolation from a subject may be limited for follow-up. The use of the peripheral blood isolated from a subject is preferred as a diagnostic sample but this should not be construed as limiting the use of the bone marrow aspirate. The "buffy coat" collected from the peripheral blood and bone marrow aspirate is a white, stripe-shaped layer located between the erythrocyte layer and the plasma layer isolated by concentration gradient centrifugation. The buffy coat essentially contains leukocytes and platelets and may further contain polymorphonuclear cells. The term "gelsolin" refers to an actin-binding protein that is known as a key regulator of actin filament assembly. The screening method of the present invention uses the level of gelsolin mRNA in the buffy coat of the subject.

(b) Measurement of the Expression Level of Gelsolin mRNA in the Buffy Coat as a Marker for a Hematologic Disease The present inventors have succeeded in demonstrating the correlation between the level of gelsolin mRNA in the buffy coat and the condition of a hematologic disease and the relevance of the profile of gelsolin mRNA levels to the relapse of the hematologic disease. Any known or future method may be used without particular limitation to measure the level of gelsolin mRNA in blood. The present invention is characterized in that the level of gelsolin mRNA in the buffy coat is used as a diagnostic marker for the hematologic disease. There is no restriction on the method for the measurement of mRNA level.

In one embodiment of the present invention, the expression level is measured by a technique selected from the group consisting of quantitative real-time PCR (qPCR), reverse transcription polymerase chain reaction (RT-PCR), rapid amplification of cDNA ends (RACE-PCR), multiplex RT-PCR, Northern blotting, nuclease protection assays, in situ hybridization, serial analysis of gene expression (SAGE), RNA microarray, RNA microarray and gene chips, and RNA sequencing (RNA-seq). Specifically, the level of gelsolin mRNA in the buffy coat may be measured by qPCR in accordance with a suitable method known in the art. qPCR was used in the Examples section that follows.

In one embodiment of the present invention, the hematologic disease is aplastic anemia or a hematologic neoplastic disease. More specifically, the hematologic neoplastic disease is selected from the group consisting of acute leukemias, chronic leukemias, myeloproliferative neoplasms, and myelodysplastic syndromes. The average gelsolin mRNA levels of biological samples (peripheral blood and/or bone marrow samples) obtained from patients with the above diseases are lower than those of healthy subjects, as confirmed by the present inventors.

The acute leukemias include, but are not limited to, acute myelogenous leukemia, acute lymphocytic leukemia, chronic myelogenous leukemia, and chronic lymphocytic leukemia. The myeloproliferative neoplasms include, but are not limited to, chronic myelogenous leukemia, polycythemia vera, essential thrombocythemia, and primary myelofibrosis. The myelodysplastic syndromes include, but are not limited to, refractory cytopenia with unilineage dysplasia, refractory cytopenia with multilineage dysplasia, refractory anemia with excess blasts-1 (RAEB-1), and refractory anemia with excess blasts-2 (RAEB-2).

According to the method of the present invention, when the expression level of gelsolin mRNA in the buffy coat is measured to be 80% or less of that in a normal group, the subject is diagnosed as being at risk of the hematologic disease. Meanwhile, when the expression level of gelsolin mRNA in the buffy coat is measured to be 120% or more of that in a normal group, the subject is diagnosed as being at risk of a hematologic neoplastic disease just before or immediately after progression to other diseases.

More specifically, the expression level of gelsolin mRNA in the buffy coat of the subject diagnosed as having the hematologic disease is 80% or less, 70% or less, 60% or less, 50% or less, 40% or less or 30% or less of that in a healthy subject. The lower expression level means the higher possibility that the subject will be diagnosed as having the hematologic disease. Particularly, the expression level of mRNA gelsolin in a leukemia patient is, on average, lower than those in myelodysplastic syndrome and myeloproliferative neoplasm patients.

In one embodiment of the present invention, the subject may be a bone marrow dysplasia patient. In this embodiment, when the mRNA expression level of gelsolin in the subject is measured to be 120% or more of that in a normal group, the bone marrow dysplasia is predicted to be progressed to a pre-leukemic stage.

In one embodiment of the present invention, the pre-leukemic stage is refractory anemia with excess blasts-2 (RAEB-2). The RAEB-2 is interpreted to include acute myelogenous leukemia (AML) immediately after development from RAEB-2.

The levels of gelsolin in most risk groups of hematologic diseases are measured to be 80% or less of those in normal groups. Exceptionally, higher gelsolin mRNA values are observed in patients during progression from a disease to another, for example, from myelodysplastic syndrome (MDS) to acute myelogenous leukemia (AML), than those observed in healthy subjects.

More specifically, the levels of gelsolin mRNA in buffy coats of patients with hematologic neoplastic diseases just before or immediately after progression to other diseases are measured to be 120% or more, 130% or more, 140% or more or 150% or more of those in healthy subjects. High levels of gelsolin mRNA are diagnostic features of patients during progression from myelodysplastic syndrome (MDS) to acute myelogenous leukemia (AML), as mentioned earlier.

In one embodiment of the present invention, the method is not affected by the level of platelets and the hemolysis of erythrocytes in the sample. Attempts have been made to use plasma gelsolin levels for disease diagnosis. However, none of the attempts were successful in obtaining consistent results because the levels of gelsolin in plasma are greatly affected by various factors, such as platelet level and erythrocyte hemolysis in samples, and sufficiently reflect the conditions of diseases, making it impossible to use the levels of gelsolin in plasma for disease diagnosis. The present inventors have found that when buffy coat isolated from peripheral blood or bone marrow is used, consistent results can be obtained irrespective of the level of platelets and the hemolysis of erythrocytes in samples. Based on this finding, the present inventors have succeeded in finding a method for the diagnosis of a hematologic neoplastic disease.

According to a further aspect of the present invention, there is provided a method for analyzing the prognosis of a hematologic neoplastic disease, including (a) measuring a first expression level of gelsolin mRNA in buffy coat of peripheral blood or a bone marrow aspirate isolated from a subject and (b) measuring a second expression level of gelsolin mRNA in another buffy coat of peripheral blood or a bone marrow aspirate isolated from the subject after the lapse of time when the condition of a disease is expected to be ameliorated and comparing the first and second expression levels wherein when the second expression level is at least 3 times higher than the first expression level, the disease is considered to be relapsed.

The present inventors have demonstrated that the current condition of a disease can be diagnosed from the expression level of gelsolin mRNA measured upon initial diagnosis of a subject and the prognosis of a disease can be analyzed through observation of the relative profile of gelsolin mRNA expression levels upon follow-up of a subject. The individual steps of the method will be explained in detail.

(a) Measurement of a First Expression Level of Gelsolin mRNA in Buffy Coat of Peripheral Blood or a Bone Marrow Aspirate Isolated from a Subject The analytical method and the diagnostic method share the use of the level of gelsolin mRNA in buffy coat in common. The same description of the diagnostic method is applicable to the analytical method and is thus omitted to avoid duplication.

The analytical method of the present invention uses two buffy coat samples isolated at different time points from a subject. As used herein, the term "first expression level" means the expression level of gelsolin mRNA in the buffy coat sample isolated earlier from a subject. The first and second expression levels of gelsolin mRNA can be represented as relative values based on the expression level of gelsolin mRNA in a healthy subject.

The first expression level can be measured by the same technique described in the diagnostic method.

(b) Measurement of a Second Expression Level of Gelsolin mRNA in Another Buffy Coat of Peripheral Blood or a Bone Marrow Aspirate Isolated from the Subject after the Lapse of Time when the Condition of a Disease is Expected to be Ameliorated and Comparison of the First and Second Expression Levels The analytical method of the present invention is to predict and prospect a change of a disease. The analytical method of the present invention optionally includes ameliorating the condition of a disease by proper treatment after measurement of the first expression level and following-up the therapeutic effect and the change of the condition. The time when the condition of a disease is expected to be ameliorated means the time taken until the condition of the disease is generally expected to be ameliorated after proper treatment and may vary depending on complex factors, such as general health of the subject, type of the treatment, and sensitivity to the treatment. The expression "time when the condition of a disease is expected to be ameliorated" considers the fact that a significant difference between the first and second expression levels is generally difficult to expect when the second expression level is measured in too short a time after measurement of the first expression level but is not necessarily premised on the amelioration of the condition. It may take several hours or even several days depending upon the kind of the disease or the therapeutic method.

Thereafter, the first expression level is compared with the second expression level. When the second expression level is about 3 times or more, 4 times or more, 5 times or more or 6 times or more higher than the first expression level, the disease is judged to be relapsed.

When the second expression level is almost the same as or lower than the first expression level, the disease is determined to respond to the treatment or to progress slowly. When the second expression level increases up to about 3 times the first expression level, the disease is not judged to be relapsed. However, when the second expression level is 5 times or more the first expression level, the disease is judged to be relapsed. In this case, for example, refractory cytopenia with multilineage dysplasia (RCMD) is judged to be relapsed into refractory anemia with excess blasts-1 (RAEB-1) or RAEB-1 is judged to be relapsed into acute myelogenous leukemia (AML) (see FIG. 3).

In one embodiment of the present invention, the buffy coat samples used in steps (a) and (b) are isolated from peripheral blood. Alternatively, the buffy coat samples may be isolated from bone marrow. However, the use of the buffy coat samples isolated from peripheral blood is preferred for the convenience of follow-up.

In one embodiment of the present invention, the expression levels are measured by a technique selected from the group consisting of quantitative real-time PCR (qPCR), reverse transcription polymerase chain reaction (RT-PCR), rapid amplification of cDNA ends (RACE-PCR), multiplex RT-PCR, Northern blotting, nuclease protection assays, in situ hybridization, serial analysis of gene expression (SAGE), RNA microarray, RNA microarray and gene chips, and RNA sequencing (RNA-seq). Specifically, the expression levels of gelsolin mRNA may be measured by the selected technique in accordance with a suitable method known in the art.

In one embodiment of the present invention, the hematologic disease is aplastic anemia or a hematologic neoplastic disease. More specifically, the hematologic neoplastic disease is selected from the group consisting of acute leukemias, chronic leukemias, myeloproliferative neoplasms, and myelodysplastic syndromes. The present inventors have demonstrated the correlation between the relapse profiles of the hematologic neoplastic diseases and the profiles of gelsolin mRNA.

According to the diagnostic method and the analytical method of the present invention, physical and economic burdens on patients can be reduced and consistent diagnostic and analytical results can be obtained without being affected by other ambient factors.

The features and advantages of the present invention are summarized as follows:

(a) the present invention is effective in screening a risk group of a hematologic disease;

(b) the present invention is effective in analyzing the prognosis of a hematologic disease;

(c) the use of the present invention enables consistent screening of a risk group of a hematologic disease while minimizing the influence of ambient factors; and (d) the use of the present invention enables the analysis of prognosis of a hematologic disease in a more accurate manner.

BRIEF DESCRIPTION OF THE DRAWINGS

FIG. 1 shows the influence of the hemolysis of peripheral blood or the incorporation of platelets on the concentration of plasma gelsolin.

FIG. 2 shows differences in the expression level of plasma gelsolin in peripheral blood and bone marrow, as measured by ELISA and qPCR.

FIG. 3 shows changes in the level of gelsolin mRNA expression in peripheral blood samples from patients with hematologic diseases.

FIG. 4 shows changes in the level of gelsolin mRNA expression in bone marrow aspirates from patients with hematologic diseases.

FIG. 5 compares the levels of gelsolin mRNA expression in peripheral blood and bone marrow of patients who were initially diagnosed as having MDS.

FIG. 6 compares the levels of gelsolin mRNA expression in peripheral blood buffy coats of patients who were initially diagnosed as having hematologic diseases.

FIG. 7 compares the levels of gelsolin mRNA expression in bone marrow buffy coats of patients who were initially diagnosed as having hematologic diseases.

MODE FOR CARRYING OUT THE INVENTION

The present invention will be explained in more detail with reference to the following examples. However, it will be obvious to those skilled in the art that these examples are provided for illustrative purposes only and are not to be construed as limiting the scope of the invention.

EXAMPLES

Experimental Methods

Example 1

Blood Collection

Bone marrow blood and peripheral blood (each about 3 ml) were collected from patients with hematologic tumors and stored in EDTA tubes. The samples were used for diagnosis within 6 h after sampling and were wasted. The samples were centrifuged at 227 g for 10 min to separate buffy coats. Leukocytes were present in the buffy coats of the peripheral blood and both leukocytes and erythroid cells were present in the buffy coats of the bone marrow. The expression levels of mRNA in the samples were measured by qPCR. All patients had no history of recent platelet and plasma transfusion to exclude the influence of blood transfusion.

Example 2

Measurement of Changes in Gelsolin Concentration after Mixing with Hemolyzed RBCs First, plasma was isolated from blood by centrifugation (227 g, 5 min, 4° C.). A RBC lysis buffer (BioLegend, San Diego, USA) was added to the plasma-free blood and allowed to stand at room temperature for 10 min. The supernatant was collected by centrifugation and stored at 4° C. For ELISA, the hemolysed blood was diluted with plasma until the total volume was 100 µl.

Example 3

Measurement of Changes in Gelsolin Concentration after Mixing with Platelets

Platelets and plasma were isolated from normal blood by centrifugation (227 g, 5 min, 4° C.). The concentrated plasma-free platelets were diluted with plasma to different platelets/plasma concentrations. At this time, the total volume was adjusted to 100 µl.

Example 4 mRNA-PCR

Buffy coat was collected from the samples by centrifugation at 227 g. Trizol (Ambion) was added to the buffy coat to extract total RNA. For RNA storage, the buffy coat was mixed with a 5-fold volume of Trizol (Choi, Lee et al. 2013); (Hofmann, de Vos et al. 2002). cDNA was synthesized using a SuperScript III Reverse Transcriptase cDNA synthesis kit (Invitrogen) and gene was amplified by qPCR using SYBR Green. All gene expression levels were measured by qPCR in duplicate and calibrated with GAPDH. The sequences of primers used in the experiments are as follows.

```
GSN,
5'-CTTTGCCTGCTCCAACAAGA-3'/    (SEQ ID NO: 2)
5'-CCGTCTCGATGTACCGCTTA-3'     (SEQ ID NO: 3)
GAPDH,
5'-GAAGGTGAAGGTCGGAGT-3'/      (SEQ ID NO: 4)
5'-GACAAGCTTCCCGTTCTCAG-3'.    (SEQ ID NO: 5)
```

Example 5

Enzyme-Linked Immunosorbent Assay (ELISA)

The concentrations of plasma gelsolin in the bone marrow and peripheral blood of patients were measured using an ELISA kit for human gelsolin (Life Science Inc., hubei, China) according to the manufacturer's manual.

The concentrations of gelsolin affected by the hemolysis of erythrocytes and the levels of plasma and platelets were measured by the following procedure. Samples containing erythrocytes dissolved at various concentrations or plasma samples containing platelets at various concentrations were placed in immune-coated 96 well plates (Nunc Immunoplates, Thermo Scientific, Germany). After standing at room temperature for 2 h, the plates were washed three times with a washing buffer (0.05% Tween20 containing PBS) and 10%

FBS in PBS was added thereto. After standing for 1 h, the plates were washed three times with a washing buffer and a primary antibody (Gelsolin antibody, Abnova, Taipei, Taiwan) was added thereto. After standing at room temperature for 1 h, the plates were washed five times with a washing buffer. Then, a secondary antibody (HRP-conjugated secondary Ab, Jackson ImmunoResearch Antibody, USA) was added and allowed to stand at room temperature for 1 h. The plates were washed seven times with a washing buffer. 30 min after addition of a detection solution (Biolegend, San Diego, Calif.), the plates were read using an ELISA reader (Applied Biosystems, Foster City, Calif.).

Example 6

Western Blotting

Plasma was isolated from bone marrow and peripheral blood collected from patients by centrifugation. Total proteins were dissolved in a lysis buffer. 20 µg of the lysate was quantified before use. Thereafter, the lysate was subjected to electrophoresis on SDS-PAGE and transferred to a Hybond-ELC nitrocellulose membrane. The protein-transferred membrane was allowed to stand in 5% skim milk (in TBST: Tris buffer saline with Tween; 25 mM Tris, 140 mM NaCl, 0.05% Tween-20, pH8.0) at room temperature for 1 h. Thereafter, a primary antibody (gelsolin, Abeam, USA) was allowed to react with the proteins at 4° C. for 12 h. The membrane was washed three times with TBST (each for 10 min) and an HRP-conjugated secondary antibody (anti-rabbit, Jackson ImmunoResearch Antibody, USA) was added thereto. After standing at room temperature for 1 h, the membrane was washed three times with TBST (each for 10 min). After addition of a detection reagent (ECL solution), the membrane was exposed to an X-ray film to identify the expression of the respective proteins.

Example 7

Statistics

The statistical significance between the disease groups was assessed using the Mann-Whitney test.

Experimental Results

1. Problems Associated with Gelsolin Level Measurement

Some patients with hematologic tumors suffer from hemolysis upon blood collection and depending on their conditions due to their weak blood vessels and erythroid dysplasia. Particularly, most bone marrow aspirate samples were accompanied by hemolysis. The levels of plasma gelsolin (pGSN) in the bone marrow and peripheral blood plasma of patients were measured by ELISA in accordance with a suitable method known in the art. Since the levels of plasma gelsolin in samples with suspected hemolysis were excessively different, the samples were not determined to reflect the actual blood gelsolin levels of patients. Also when the plasma gelsolin levels were measured by Western blotting, the results showed large differences depending on the degree of incorporation of RBCs and it was, therefore, impossible to measure the actual pGSN levels. Thus, the present inventors have found for the first time that the levels of plasma gelsolin in hemolyzed samples may fluctuate very much.

As a result, the present inventors were aware that the exact pGSN concentrations cannot be measured until no hemolysis in samples is confirmed every time (FIG. 1). The present inventors have also found that the plasma gelsolin level is affected by an increase in the amount of platelet incorporated. Accordingly, it could be concluded that measurement of the levels of pGSN in plasma by ELISA or measurement of the levels of gelsolin in leukocytes by Western blotting after isolation of buffy coat and mononuclear cells is not appropriate for the examination of general patient samples.

The left panel of FIG. 1 shows the concentrations of gelsolin in mixtures of hemolysed RBCs and hemolysis-free plasma in given proportions in order to confirm the influence of hemolysis, which is common when collection of peripheral blood and bone marrow blood, on the concentration of gelsolin in plasma. The gelsolin concentrations were measured by ELISA. As the amount of the hemolysed RBCS increased, the gelsolin concentration increased, demonstrating that the plasma gelsolin concentration was greatly affected by hemolysis. The right panel of FIG. 1 shows the concentrations of gelsolin in mixtures of platelets and plasma in different dilution ratios. The gelsolin concentrations were measured by ELISA. The plasma gelsolin concentration decreased with increasing platelet dilution ratio, demonstrating the relevance of the increased concentration of platelets in plasma to the gelsolin concentration.

The abbreviations used in the drawings and tables are shown in Table 1.

TABLE 1

| | |
|---|---|
| PB | Peripheral blood |
| BM | Bone marrow |
| MDS | Myelodysplastic syndrome |
| PLT | Platelet |
| RA | Refractory anemia |
| RCMD | Refractory cytopenia with multilineage dysplasia |
| RCMD-RS | RCMD with ringed sideroblasts |
| RAEB-1 | Refractory anemia with excess blasts-1 |
| RAEB-2 | Refractory anemia with excess blasts-2 |
| CMML | Chronic myelomonocytic leukemia |
| AML | Acute myeloid leukemia |
| AMML | Acute myelomonocytic leukemia |
| ALL | Acute lymphoblastic leukemia |
| CLL | Chronic lymphoblastic leukemia |
| APL | Acute promyelocytic leukemia |
| MPN | Myeloproliferative neoplasms |
| CML | Chronic myelogenous leukemia |
| P-vera | Polycythemia vera |
| ET | Essential thrombocythemia |
| AA | Aplastic anemia |
| CR | Complete remission |

2. Significance of Measurement of mRNA in Buffy Coat

Generally, the concentration of protein and the level of mRNA expression do not have the same meaning. The present inventors have measured for the first time the concentration of gelsolin in buffy coat at a molecular level instead of the concentration of protein, which is affected by the concentration of platelets and hemolysis of erythrocytes in samples. The level of gelsolin in buffy coat was thought to be more consistent than the level of plasma protein affected by other factors of samples and become an indicator rapidly reflecting the condition of disease.

Thus, the present inventors have conducted experiments to determine whether the expression level of gelsolin mRNA in buffy coat containing platelets as well as blood leukocytes and erythroblasts from blood and bone marrow of patients with hematologic neoplastic diseases, including myelodysplastic syndromes and acute or chronic leukemia, is of significance in the diagnosis and the analysis of prognosis of the diseases. Particularly, this examination method is simple to perform and minimizes errors between operators compared to methods based on the isolation of mononuclear cells by density gradient centrifugation, which are difficult to use in clinical laboratory, demonstrating its high applicability.

Hemolysis of bone marrow aspirates is common in patients with hematologic neoplastic diseases compared to in normal groups. Accordingly, the levels of mRNA in bone marrow aspirates from patients with hematologic neoplastic diseases were higher than those from healthy subjects, as measured by ELISA. In contrast, the levels of mRNA in buffy coat of patients with hematologic neoplastic diseases were mostly lower than those of healthy subjects, as examined by qPCR.

3. Changes in the Expression Level of Gelsolin mRNA in Peripheral Blood According to Disease Progression In peripheral blood samples from 11 patients with myelodysplastic syndromes and hematologic neoplastic diseases, the correlation between the conditions of the diseases and the expression of gelsolin was examined. In FIG. 3, the bars of the same type indicate the results obtained from the same patient and the Y-axis shows changes in the condition of the diseases with the passage of time.

The expression levels of gelsolin mRNA in the samples were lower by an average of 86.6-fold (425.7~4.3-fold) at follow-up than at initial diagnosis. Cases 2, 3, 4, 5, and 9 responded to the treatment and showed slow disease progression. Although the expression levels of Cases 1 and 5 were 3.4 and 2.1 times higher than the respective initial values, no relapse of the diseases was found. In contrast, the mRNA values of some cases increased by 5 times or more after the initial diagnosis. They did not respond to the treatment and were relapsed. Specifically, Case 6 (6.2-fold) was relapsed from RCMD into RAEB-1 or Case 7 (6.7-fold) was relapsed from RAEB-1 into AML. Case 8 (11.4-fold) who had received chemotherapy after relapse from myelodysplastic syndrome into AML showed a reduced gelsolin value. Thereafter, Case 8 did not respond to the treatment and finally died. Case 10 who had been diagnosed as ALL effectively responded to the treatment and was completely cured. Thereafter, reoccurrence of the disease was detected in Case 10. At this time, the expression level of gelsolin mRNA in Case 10 increased by 5.1 times. To sum up, when MDS and acute leukemia was relapsed, the expression levels of gelsolin mRNA increased significantly by an average of 7.36-fold (5.1~11.4-fold). Case 11 had suffered from a solid cancer of unknown origin that metastasized into bone marrow. The gelsolin level of Case 11 decreased sharply just before death, unlike those of the patients with hematologic neoplastic diseases.

In summary, gelsolin mRNA profiles in buffy coat of peripheral blood from patients with hematologic neoplastic diseases, such as myelodysplastic syndromes and leukemia, are useful as diagnostic and prognostic factors for the treatment and relapse of the diseases, demonstrating their possible use as prognostic factors for the progression of hematologic neoplastic diseases, particularly, myelodysplastic syndromes.

4. Changes in the Expression Level of Gelsolin mRNA in Bone Marrow

Bone marrow samples were collected from 5 patients with myelodysplastic syndromes and hematologic neoplastic diseases in the same manner as in the peripheral blood collection. The bone marrow samples were used for clinical follow-up to examine the correlation between gelsolin expression and the diseases. In FIG. 4, the bars of the same type indicate the samples of the same patient and the Y-axis shows changes in the condition of the diseases with the passage of time.

The increased or decreased expression levels of gelsolin in the bone marrow samples were confirmed to be similar to those in the peripheral blood samples. Case 8 showed decreased cellularity of bone marrow after chemotherapy, leading to a remarkable reduction in the expression level of gelsolin. The expression levels of gelsolin in Case 5 and Case 13 increased by only 3.2- and 3.3-fold, respectively. Case 12 who had recovered from CML after diagnosis showed a decreased expression level of gelsolin.

The myelodysplastic syndrome and leukemia groups were compared using Case 14 with aplastic anemia (AA). Case 14 had a low value and showed no significant change even after initial diagnosis. These results, together with the results of the peripheral blood examination, reveal that increased or decreased expression levels of gelsolin mRNA are helpful in determining the effects on the treatment of hematologic neoplastic diseases, particularly myelodysplastic syndromes and leukemia, and the progression and relapse of the diseases.

The left panel of FIG. 5 shows low expression levels of gelsolin in the PB samples of patients with myelodysplastic syndromes RA, RCMD, and RAEB-1 corresponding to low/intermediate states (medians were 0.07, 0.49, and 0.49 for RA, RCMD, and RAEB-1, respectively). In contrast, the RAEB-2 patients showed higher values (median 2.38) than healthy subjects. 33% of the RAEB-2 patients were relapsed into leukemia within 18 months. These results are in good agreement with the increased gelsolin values when the diseases were relapsed upon follow-up diagnosis using peripheral blood from the patients (FIG. 3).

The right panel of FIG. 5 shows lower expression levels of gelsolin in the BM samples of patients with MDS-RA, RCMD, and RAEB-1 than those of normal groups (medians were 0.09, 0.83, and 0.80 for RA, RCMD, and RAEB-1, respectively). In contrast, the median for RAEB-2 was higher (1.63) than that for the normal group. Considering the increased expression levels of gelsolin in RAEB-2, which is considered a preliminary stage of acute leukemia, the expression of gelsolin mRNA would be an auxiliary criterion in determining the relapse of the disease.

5. Expression Levels of Gelsolin mRNA in Buffy Coat of Peripheral Blood

The expression levels of gelsolin mRNA in peripheral blood samples collected from 5 different patient groups with myelodysplastic syndromes (MDS) and hematologic neoplastic diseases, including leukemia, lymphoma, myeloproliferative neoplasm (MPN), etc., upon initial diagnosis were measured by qPCR and compared with that ("1") in healthy subjects. The sub-diseases and the number of cases are shown in Table 2.

TABLE 2

| Group | Diagnosis | Number of cases |
| --- | --- | --- |
| Healthy donor | — | 3 |
| MDS | RA | 1 |
| | RCMD | 6 |
| | RAEB-1 | 3 |
| | RAEB-2 | 2 |
| Leukemia | AML | 5 |
| | AMML | 2 |
| | ALL | 2 |
| | CLL | 2 |
| | APL | 2 |
| | Peripheral T-cell leukemia | 2 |

TABLE 2-continued

| Group | Diagnosis | Number of cases |
|---|---|---|
| BM involvement of lymphoma | NK/T cell lymphoma, Follicular lymphoma | 1 1 |
| Myeloproliferative neoplasm (MPN) | CML ET P-vera | 4 2 1 |
| Etc. | Aplastic anemia Thrombotic thrombocytopenic purpura (TTP) Associated with BM of metastatic cancer premature babies | 3 1 1 1 |

The MDS, leukemia, lymphoma, and MPN groups showed lower median expression levels of gelsolin mRNA than the healthy subjects. Particularly, the leukemia group had a lower median and was statistically significantly different from the other groups (P values were 0.016, 0.040, and 0.005 for MDS, MPN, and etc., respectively) (see FIG. 6). Irrespective of whether the diseases were acute or chronic or myeloid or lymphoid, the expression levels of gelsolin were very low in all of the AML, ALL, and CLL groups.

Very low expression levels of gelsolin were also observed in the MPN group, including essential thrombocythemia (ET) accompanied by an increased number of platelets and polycythemia vera (PV) accompanied by increased numbers of erythrocytes and bone marrow cells as well as CML accompanied by an increased number of leukocytes, erythrocytes or platelets. These results indicate that an increased number of blood cells, including platelets, does not simply lead to an increase in the expression level of gelsolin mRNA. Relapse of CML led to a significant increase in the expression level of gelsolin.

In the Etc group, the expression levels of gelsolin mRNA were low for aplastic anemia, a disease where few cells are present in bone marrow, and hypocellular marrow. The expressions of gelsolin mRNA in premature babies were high compared to those in healthy adults.

Considering that the expression levels of gelsolin in acute leukemia were very significantly low compared to those in the MDS group, it is determined that the expression level of gelsolin would be helpful in screening and diagnosing MDS, particularly RAEB-2, that progresses to acute leukemia.

6. Comparison of Expression Levels of Gelsolin mRNA in Buffy Coat of Bone Marrow The expression levels of gelsolin mRNA in bone marrow aspirates collected from 5 different patient groups with myelodysplastic syndromes (MDS) and hematologic neoplastic diseases, including leukemia, lymphoma, myeloproliferative neoplasm (MPN), etc., for initial diagnosis were measured by qPCR and compared with that ("1") in healthy subjects. The patient groups were divided through bone marrow examination. The sub-diseases are shown in Table 2.

TABLE 3

| Group | Diagnosis | Number of cases |
|---|---|---|
| Healthy donor | — | 2 |
| MDS | RA | 2 |
|  | RCMD | 4 |
|  | RAEB-1 | 5 |
|  | RAEB-2 | 2 |
| Leukemia | AML | 5 |
|  | AMML | 1 |
|  | ALL | 2 |
|  | CLL | 1 |
|  | APL | 1 |
|  | Peripheral T-cell leukemia | 1 |

TABLE 3-continued

| Group | Diagnosis | Number of cases |
|---|---|---|
| BM involvement of lymphoma | NK/T cell lymphoma | 3 |
| Myeloproliferative neoplasm (MPN) | CML ET P-vera | 5 3 3 |
| Etc. | Aplastic anemia Thrombotic thrombocytopenic purpura (TTP), Associated with BM of metastatic cancer premature babies | 1 1 1 4 |

The expression levels and profiles of gelsolin mRNA in the bone marrow samples were similar to those in the peripheral blood samples. The MDS, leukemia, lymphoma, and MPN groups showed lower expression levels of gelsolin mRNA than the healthy subjects. Particularly, the leukemia group had a lower median and was significantly different from the other groups (P values were 0.024, 0.030, and 0.019 for MDS, MPN, and Etc., respectively) (see FIG. 7). As in the results obtained in the peripheral blood samples, the leukemia group, including AML, ALL, and CLL, showed very low expression levels of gelsolin (median 0.05). The patients with bone marrow involvement of lymphoma showed low expression levels of gelsolin mRNA (median 0.12) when diagnosed. Particularly, like the results obtained in the peripheral blood samples, low gelsolin levels were observed in the MPN group, including CML, P-vera, and ET, which are diseases accompanied by significantly increased numbers of leukemic cells, erythroid cells, and platelets. The gelsolin levels in aplastic anemia and hypocellular marrow belonging to the Etc group showed a tendency to decrease. These results are contrary to the results obtained in the peripheral blood samples. The expression levels of gelsolin in aplastic anemia (AA) as a hematologic disease were lower (0.36+/−0.18) than the control. Therefore, in the hematologic neoplastic diseases with bone marrow involvement that do not belong to the Etc group, the same expression patterns of gelsolin mRNA were obtained in both peripheral blood and bone marrow for the respective diseases. In conclusion, this method enables precise tracing of the progress of hematologic neoplastic diseases using peripheral blood collected for regular examination, compared to conventional methods requiring invasive bone marrow collection only when a diagnosis is made.

In the present invention, buffy coat of bone marrow or peripheral blood was used to demonstrate the correlation between the expression of gelsolin mRNA and diseases. Based on this correlation, it can be conclude that the expression of gelsolin mRNA is useful as a marker or can be used for the treatment of diseases.

While specific embodiments of the invention have been described in detail, it will be appreciated by those skilled in the art that such detailed descriptions are merely preferred embodiments and the scope of the present invention is not limited thereto. Therefore, the true scope of the present invention should be defined by the appended claims and their equivalents.

REFERENCES

Barzi, A. and M. A. Sekeres (2010). "Myelodysplastic syndromes: a practical approach to diagnosis and treatment." Cleve Clin J Med 77 (1): 37-44.

Braoudaki, M., G. I. Lambrou, K. Vougas, K. Karamolegou, G. T. Tsangaris and F. Tzortzatou-Stathopoulou (2013). "Protein biomarkers distinguish between high- and low-risk pediatric acute lymphoblastic leukemia in a tissue specific manner." J Hematol Oncol 6 (52): 1756-8722.

Brunning R D, O. A., Germing U, Le Beau M M, et al., Ed. (2008). Myelodysplastic syndromes/neoplasms, overview. In: Swerdlow S H, Campo E, Harris N L, et al. eds., WHO Classification of Tumours of Hematopoietic and Lymphoid Tissues., Lyon, France, IARC Press.

Chauhan, V., L. Ji and A. Chauhan (2008). "Anti-amyloidogenic, anti-oxidant and anti-apoptotic role of gelsolin in Alzheimer's disease." Biogerontology 9 (6): 381-389.

Choi, H. S., E. M. Lee, H. O. Kim, M. I. Park and E. J. Baek (2013). "Autonomous control of terminal erythropoiesis via physical interactions among erythroid cells." Stem Cell Res 10 (3): 442-453.

Gremm, D. and A. Wegner (2000). "Gelsolin as a calcium-regulated actin filament-capping protein." Eur J Biochem 267 (14): 4339-4345.

Hofmann, W. K., S. de Vos, M. Komor, D. Hoelzer, W. Wachsman and H. P. Koeffler (2002). "Characterization of gene expression of CD34+ cells from normal and myelodysplastic bone marrow." Blood 100 (10): 3553-3560.

Kwiatkowski, D. J. (1988). "Predominant induction of gelsolin and actin-binding protein during myeloid differentiation." J Biol Chem 263 (27): 13857-13862.

Lee, W. M. and R. M. Galbraith (1992). "The extracellular actin-scavenger system and actin toxicity." N Engl J Med 326 (20): 1335-1341.

Newman, K., L. Maness-Harris, I. El-Hemaidi and M. Akhtari (2012). "Revisiting use of growth factors in myelodysplastic syndromes." Asian Pac J Cancer Prev 13 (4): 1081-1091.

Noske, A., C. Denkert, H. Schober, C. Sers, B. Zhumabayeva, W. Weichert, M. Dietel and K. Wiechen (2005). "Loss of Gelsolin expression in human ovarian carcinomas." Eur J Cancer 41 (3): 461-469.

Qi, X., Z. Chen, J. Qian, J. Cen and M. Gu (2008). "Expression of Rap1GAP in human myeloid disease following microarray selection." Genet Mol Res 7 (2): 379-387.

Suhler, E., W. Lin, H. L. Yin and W. M. Lee (1997). "Decreased plasma gelsolin concentrations in acute liver failure, myocardial infarction, septic shock, and myonecrosis." Crit Care Med 25 (4): 594-598.

Vardiman J W, M. J., Baccarani M, et al., Ed. (2008). Introduction and overview of the classification of the myeloid neoplasms. In: Vardiman J W, Brunning R D, Arber D A, Le Beau M M. eds., WHO Classification of Tumours of Hematopoietic and Lymphoid Tissues., Lyon, France, IARC Press.

The invention claimed is:

1. A method comprising:
   (a) providing buffy coat of peripheral blood or buffy coat of a bone marrow aspirate isolated from a subject, and
   (b) measuring the expression level of gelsolin mRNA in the buffy coat,
   wherein the expression level is measured by a technique selected from the group consisting of quantitative real-time PCR (qPCR), reverse transcription polymerase chain reaction (RT-PCR), rapid amplification of cDNA ends (RACE-PCR), multiplex RT-PCR, Northern blotting, nuclease protection assays, in situ hybridization, serial analysis of gene expression (SAGE), and RNA sequencing (RNA-seq).

2. The method according to claim 1, wherein the subject is a bone marrow dysplasia patient.

3. The method according to claim 1, wherein the method is not affected by the level of platelets and the hemolysis of erythrocytes in the sample.

* * * * *

SEQUENCE LISTING

```
<160> NUMBER OF SEQ ID NOS: 5

<210> SEQ ID NO 1
<211> LENGTH: 2349
<212> TYPE: DNA
<213> ORGANISM: Homo sapiens

<400> SEQUENCE: 1
atggctccgc accgcccgc gcccgcgctg ctttgcgcgc tgtccctggc gctgtgcgcg      60
ctgtcgctgc ccgtccgcgc ggccactgcg tcgcgggggg cgtcccaggc gggggcgccc     120
caggggcggg tgcccgaggc gcggcccaac agcatggtgg tggaacaccc cgagttcctc     180
aaggcaggga aggagcctgg cctgcagatc tggcgtgtgg agaagttcga tctggtgccc     240
gtgcccacca acctttatgg agacttcttc acgggcgacg cctacgtcat cctgaagaca     300
gtgcagctga ggaacggaaa tctgcagtat gacctccact actggctggg caatgagtgc     360
agccaggatg agagcggggc ggccgccatc tttaccgtgc agctggatga ctacctgaac     420
ggccgggccg tgcagcaccg tgaggtccag ggcttcgagt cggccacctt cctaggctac     480
ttcaagtctg gcctgaagta caagaaagga ggtgtggcat caggattcaa gcacgtggta     540
cccaacgagg tggtggtgca gagactcttc caggtcaaag ggcggcgtgt ggtccgtgcc     600
accgaggtac ctgtgtcctg ggagagcttc aacaatggcg actgcttcat cctggacctg     660
ggcaacaaca tccaccagtg gtgtggttcc aacagcaatc ggtatgaaag actgaaggcc     720
acacaggtgt ccaagggcat ccgggacaac gagcggagtg gccgggcccg agtgcacgtg     780
tctgaggagg gcactgagcc cgaggcgatg ctccaggtgc tgggcccaa gccggctctg     840 cctgcaggta ccgaggacac cgccaaggag gatgcggcca accgcaagct ggccaagctc     900
tacaaggtct ccaatggtgc agggaccatg tccgtctccc tcgtggctga tgagaacccc     960
ttcgcccagg gggcctgaa gtcagaggac tgcttcatcc tggaccacgg caagatggg    1020 aaaatctttg tctggaaagg caagcaggca aacacggagg agaggaaggc tgccctcaaa    1080
```

```
acagcctctg acttcatcac caagatggac taccccaagc agactcaggt ctcggtcctt   1140
cctgagggcg gtgagacccc actgttcaag cagttcttca agaactggcg ggacccagac   1200
cagacagatg gcctgggctt gtcctacctt tccagccata tcgccaacgt ggagcgggtg   1260
cccttcgacg ccgccaccct gcacacctcc actgccatgg ccgcccagca cggcatggat   1320
gacgatggca caggccagaa acagatctgg agaatcgaag gttccaacaa ggtgcccgtg   1380
gaccctgcca catatggaca gttctatgga ggcgacagct acatcattct gtacaactac   1440
cgccatggtg gccgccaggg gcagataatc tataactggc agggtgccca gtctacccag   1500
gatgaggtcg ctgcatctgc catcctgact gctcagctgg atgaggagct gggaggtacc   1560
cctgtccaga gccgtgtggt ccaaggcaag gagcccgccc acctcatgag cctgtttggt   1620
gggaagccca tgatcatcta caagggcggc acctcccgcg agggcgggca gacagcccct   1680
gccagcaccc gcctcttcca ggtccgcgcc aacagcgctg gagccacccg ggctgttgag   1740
gtattgccta aggctggtgc actgaactcc aacgatgcct ttgttctgaa aaccccctca   1800
gccgcctacc tgtgggtggg tacaggagcc agcgaggcag agaagacggg ggcccaggag   1860
ctgctcaggg tgctgcgggc ccaacctgtg caggtggcag aaggcagcga gccagatggc   1920
ttctgggagg ccctgggcgg gaaggctgcc taccgcacat ccccacggct gaaggacaag   1980
aagatggatg cccatcctcc tcgcctcttt gcctgctcca acaagattgg acgttttgtg   2040
atcgaagagg ttcctggtga gctcatgcag gaagacctgg caacggatga cgtcatgctt   2100
ctggacacct gggaccaggt ctttgtctgg gttggaaagg attctcaaga agaagaaaag   2160
acagaagcct tgacttctgc taagcggtac atcgagacgg acccagccaa tcgggatcgg   2220
cggacgccca tcaccgtggt gaagcaaggc tttgagcctc cctcctttgt gggctggttc   2280
cttggctggg atgatgatta ctggtctgtg gaccccttgg acagggccat ggctgagctg   2340
gctgcctga                                                           2349
```

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
ctttgcctgc tccaacaaga                                                20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
ccgtctcgat gtaccgctta                                                20

<210> SEQ ID NO 4
<211> LENGTH: 18
<212> TYPE: DNA
<213> ORGANISM: Artificial Sequence
<220> FEATURE:
<223> OTHER INFORMATION: Synthetic primer

<400> SEQUENCE: 4
gaaggtgaag gtcggagt                                                  18

```
<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
gacaagcttc ccgttctcag                                              20
```